United States Patent [19]
Reid et al.

[11] Patent Number: 5,688,916
[45] Date of Patent: Nov. 18, 1997

[54] HUMAN CELL ADHESION MOLECULE

[75] Inventors: Robert Alan Reid, Durham; John Jacob Hemperly, Apex, both of N.C.

[73] Assignee: Becton, Dickinson and Company, Franklin Lakes, N.J.

[21] Appl. No.: 408,093

[22] Filed: Mar. 21, 1995

Related U.S. Application Data

[62] Division of Ser. No. 40,741, Mar. 26, 1993.

[51] Int. Cl.$^6$ .......................... C07K 14/705; A61K 38/00
[52] U.S. Cl. .......................... 530/350; 530/300; 536/23.5
[58] Field of Search ...................................... 530/350, 300; 536/23.5

[56] References Cited

PUBLICATIONS

Berglund et al. (1991) Eur. J. Biochem, 197: 549–554.
Walsh and Doherty (1991) Cell Bio. Int. Rep. 15: 1151–1166.
Reid et al, (1994) Molec. Brain Res. 21: 1–8.
Berglund and Ranscht (1994) Genomics 21: 571–582.

*Primary Examiner*—Stephen Walsh
*Assistant Examiner*—Kenneth A. Sorensen
*Attorney, Agent, or Firm*—Donna R Fugit

[57] ABSTRACT

A human brain glycoprotein homologous to the mouse F3 and the chicken contactin/F11 adhesion molecules, nucleic acid sequences encoding the human brain glycoprotein and antibodies directed against the human brain glycoprotein.

5 Claims, 1 Drawing Sheet

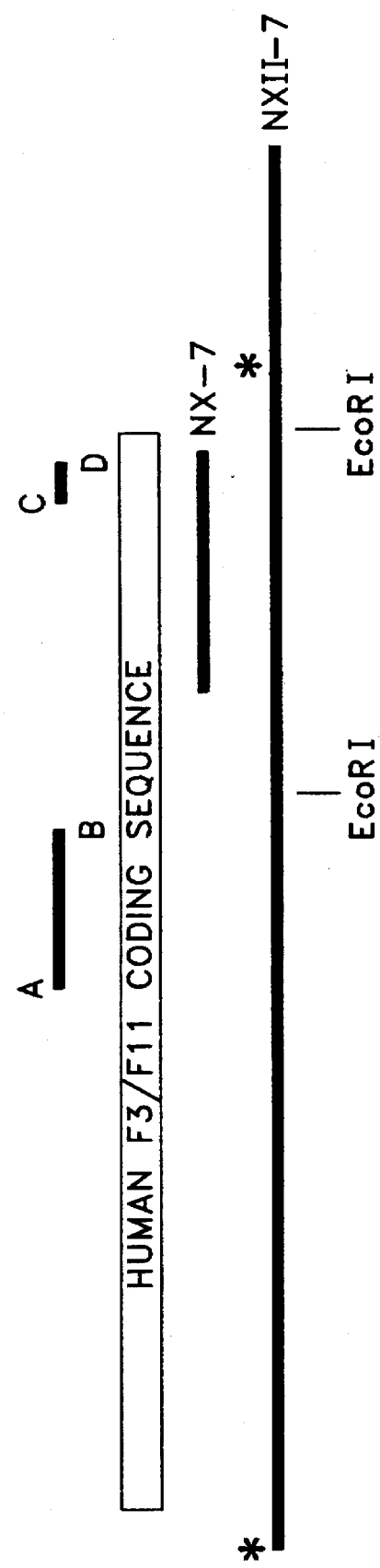

HUMAN CELL ADHESION MOLECULE

This is a division of application Ser. No. 08/040,741, filed Mar. 26, 1993.

FIELD OF THE INVENTION

The present invention relates to cell adhesion molecules and nucleic acid sequences which code for cell adhesion molecules. In particular, the invention pertains to human cell adhesion molecules and nucleic acid sequences which code therefor.

BACKGROUND OF THE INVENTION

Adhesion between cells plays an essential role in development and maintenance of tissue form and function. Intercellular adhesion is mediated by a class of adhesive cell surface proteins commonly referred to as "cell adhesion molecules" or "CAMs". These proteins have been identified and characterized in a phylogenetically diverse range of organisms and have been found in many cases to be highly conserved in structure. Certain cell surface CAMs are members of a superfamily of glycoproteins which are structurally related to immunoglobulins, i.e., their structure contains a number of extracellular immunoglobulin-like and fibronectin Type III-like domains.

The immunoglobulin superfamily of CAMs includes the neural cell adhesion molecule (N-CAM), the L1 antigen, Ng-CAM, TAG-1, and others. These CAMs are believed to mediate homophilic binding between cells and have also recently been recognized as participants in heterophilic interactions with other cell surface molecules, extracellular matrix proteins and proteoglycans. Many are also believed to be involved in transmission of signals to the interior of the cell Which modulate cell morphology, cell metabolism and cell adhesion. The means by which these molecules transmit signals to the interior of the cell is unclear.

The F11 antigen (F11) is a chicken neural cell surface-associated glycoprotein which is believed to be involved in neurite-neurite interactions. The cDNA sequence of F11 has been determined and it codes for a 1010 amino acid protein (Brümmendoff, et al. (1989) Neuron 2:1351–1361). The F11 molecule comprises six domains related to the immunoglobulin domain type C and four domains similar to the fibronectin Type III repeat. These structures are also present in L1 and N-CAM. The cDNA sequence of F11 was found to be almost identical to the cDNA sequence of the chicken neural glycoprotein contactin (Ranscht, et al. (1988) J. Cell Biol. 107:1561–1573; Zisch, et al. (1992) J. Cell Biol. 119:203–213) and it is now believed that the molecules are the same (contactin/F11). However, prior to Applicants' invention, the identity was not clear. A mouse neural cell surface protein, F3, has been identified and is the homologue of the chicken neuronal cell adhesion protein contactin/F11. The cDNA which codes for F3 has been cloned and sequenced, revealing an open reading frame encoding a 1020 amino acid protein having the characteristics of the immunoglobulin superfamily (G. Gennarini, et al. 1989. J. Cell Biol. 109:775–788).

The present invention relates to CAMs involved in human neural cell adhesion. Specifically, the present invention provides the purification and characterization of the human counterpart of the mouse F3 and chicken contactin/F11 proteins, the preparation of monoclonal and polyclonal antibodies to the human contactin and nucleic acid sequences encoding the human contactin. E. Berglund, et al. (1987. J. Neurochem. 48:809–815) have used monoclonal antibodies to characterize glycoproteins in human brain and have reported isolation and characterization of a molecule identified as Gp135 (E. Berglund, et al. 1991. Eur. J. Biochem. 197:549–554; E. Berglund, et al. 1991. Brain Res. 549:292–296). These authors sequenced the amino terminus of the protein and an internal peptide. On the basis of these sequences they identified a similarity to chicken contactin/F11 and mouse F3, however, the reported amino acid sequence of Gp135 is different from that of the human contactin molecule described herein. It was therefore also unclear prior to Applicants' invention whether or not human Gp135 was the direct homolog of F3, contactin/F11. E. Berglund and B. Ranscht later reported the isolation and partial characterization of cDNA clones encoding Gp135 (1992. Soc. Neurosci. Abst. 18:1325, Abst. #560.5).

SUMMARY OF THE INVENTION

Using monoclonal antibodies, a human brain glycoprotein (human contactin) homologous to the mouse F3 and the chicken contactin/F11 adhesion molecules has been isolated and characterized. A complete coding sequence of the human contactin gene has been determined by sequencing of human neuroblastoma cDNA clones. The gene could potentially encode other, alternatively spliced complete coding regions as well. At the nucleotide level, the human cDNA is 86% homologous to the mouse F3 cDNA. The deduced amino acid sequences are 95% homologous and predict several common structural features, including six immunoglobulin-like and four fibronectin Type III-like domains, as well as multiple sites for Asn-linked glycosylation. The mouse, chicken and human glycoproteins all contain carboxy-terminal hydrophobic segments which may be important for linking the proteins to the cell surface via a phosphatidylinositol anchor.

The human contactin glycoprotein is approximately 135 kD molecular weight and may be purified by immunoaffinity methods using monoclonal antibodies. Partial sequencing of an internal peptide yielded an amino acid sequence identical to that predicted from the cDNA. The cDNA has been expressed in recombinant host microorganisms and the gene product has been shown to be immunoreactive with polyclonal antisera raised against the monoclonal antibody-purified human contactin antigen. Northern blot analyses of the RNAs of various human tissues demonstrated a single major approximately 6.5 kb human contactin transcript in adult brain. Multiple transcripts (6.8 kb, a 6.0 kb doublet and 4.2 kb) are expressed in retinoblastoma and neuroblastoma cell lines. A low level expression of approximately 6.8 and 6.0 kb transcripts, similar to those observed in transformed cell lines, was also detected in human lung and pancreas. Very weak 6.8 and 6.0 kb bands were seen in kidney and skeletal muscle.

DESCRIPTION OF THE DRAWINGS

FIG. 1 illustrates the relationships of the mouse F3 probes used to clone the human contactin cDNA, the cDNAs carried in the NX-7 and NXII-7 clones and the human contactin coding sequence.

DETAILED DESCRIPTION OF THE INVENTION

The human contactin cell adhesion protein of the invention may be isolated from any human neural tissue in which it is expressed. The preferred source is human brain tissue. While conventional chemical and biochemical methods for isolation may be employed, the human contactin cell adhesion protein is most preferably isolated by immunoaffinity methods using antibodies which recognize and bind to it. Immunoaffinity methods for isolating antigens are well known in the art and may be employed to isolate the human contactin of the present invention using the appropriate monoclonal or polyclonal antibody which recognizes the human contactin molecule. Monoclonal antibodies such as the CF3 antibody described by E. Berglund, et al., supra, or the Neuro-1 antibody described below are preferred, the Neuro-1 antibody being most preferred for isolation of the human contactin protein.

Monoclonal antibodies which recognize the human contactin protein of the invention may be prepared using the methods of Kohler and Milstein ((1975) Nature 256:495) as is known in the art. The preferred antigen for immunization is a preparation of adult human brain membranes and the most preferred antigen is a synaptosomal fraction of these membranes which is enriched for cell surface glycoproteins. Mice may be immunized with the antigen preparation, the spleen cells fused and the resulting hybridomas screened against the original immunogen to select hybridomas.

Using these methods, a hybridoma which produces the monoclonal antibody herein designated Neuro-1 was identified. A crude synaptosomal membrane fraction was prepared from adult human brain tissue (Carlin, R. K., et al. (1980) J. Cell. Biol. 86:831–843)). Membrane glycoproteins were extracted with TERGITOL Type NP-40 (polyglycol ether surfactant, Union Carbide Corp.) and separated by affinity chromatography on immobilized lentil lectin (Pharmacia Biotech, Inc., Piscataway, N.J.) to yield a crude brain glycoprotein fraction. This material was used to immunize C57BL/6 mice (40 µg/mouse). Lymph nodes from animals having the highest serum titers against the immunogen were fused with PcX63Ag8.653 cells (Goding, J. W. (1980) J. Immun. Meth. 39:285–308; ATCC CRL 1580). The resulting hybridomas were screened in enzyme-linked immunosorbent assays (ELISAs) for reactivity with the immunogen and tested for reactivity in immunoblots. A hybridoma secreting an antibody designated Neuro-1 was subcloned by limiting dilution. The Neuro-1 monoclonal antibody was produced in ascites in pristane-primed Balb/C mice and purified by chromatography on Protein A-Sepharose (Sigma Chemical Co., St. Louis, Mo.).

Neuro-1, isotype IgG2b, reacts strongly with the original immunogen in enzyme-linked immunosorbent assays (ELISAs) and recognizes an approximately 135 kD polypeptide on immunoblots. Occasionally, the Neuro-1 antigen appears on immunoblots as a closely spaced doublet. The Neuro-1 producing hybridoma has been deposited with the American Type Culture Collection (Rockville, Md.) on Mar. 3, 1993 under the Accession Number HB 11282 and it is the preferred monoclonal antibody for isolation and characterization of the human contactin cell adhesion molecule.

Neuro-1 monoclonal antibody was coupled to Protein A-Sepharose using methyl piperimidate (Harlow, E. and Lane, D. (1988) *Antibodies: A Laboratory Manual*, Cold Spring Harbor Press, p. 522). The membrane extracts described above were then passed over the affinity column and the bound antigen eluted using 0.1M diethylamine, pH 11.5. The eluted material was concentrated by binding to diethylaminoethyl cellulose (Whatman DE52, Fisher Scientific, Pittsburgh, Pa.) in 0.01M Tris-HCl and eluted with 1M NaCl. It was found that if frozen membrane extracts were used in the isolation procedure the Neuro-1 antigen tended to become insoluble. In these cases, the precipitated material was solubilized in deoxycholate, dialyzed against NP40-containing column buffer and processed as above.

Polyclonal antibodies were generated by immunizing animals with the material bound and eluted from immobilized Neuro-1 affinity columns. The polyclonal antibodies were further enriched by chromatography on an immobilized Neuro-1 antigen affinity column.

The 135 kD Neuro-1 antigen was characterized by binding to lentil lectin-Sepharose and elution with glucose, indicating that the polypeptide is glycosylated. The presence of asparagine-linked carbohydrate was verified by treating the antigen with endoglycosidase F (Genzyme, Cambridge, Mass.) and showing a shift to a lower molecular weight. The antigen was found to be released from the cell surface by phosphatidylinositol-specific phospholipase C, indicating that the molecule is anchored to the surface by a lipid linkage. These analyses were performed by washing crude human brain synaptosomal membrane preparations and suspending them in 0.02M NaOAc, pH 6.0. The enzyme was added and the samples were incubated for 4 hours at 37° C. The membranes were collected by centrifugation and equivalent amounts of membranes and supernatants were analyzed by immunoblotting. Treatment of the reaction mixtures with zinc or with o-phenanthrolene showed inhibition and no inhibition of release, respectively. Both polypeptides of the doublet seen on immunoblots were released by phospholipase C treatment, so it is believed that they do not represent anchored and endogenously released forms of the human contactin molecule.

The amino terminal sequence and the sequence of an internal peptide of the Neuro-1 antigen were determined and compared to the published amino acid sequences of mouse F3 and chicken contactin/F11. Amino terminal sequences were determined using immunoaffinity purified material blotted to IMMOBILON-P (Pall Corp., Glen Cove, N.Y.). The amino terminal sequence data were difficult to interpret and contained a large number of unassigned residues. Although many of these ambiguities involved amino acids which are sometimes difficult to detect by sequence analysis, it is also possible that proteolysis of the molecule creates heterogeneity at the amino terminus. Internal peptides were generated by cleavage with endopeptidase lys-c, separated by HPLC and sequenced. The sequence of the internal peptide was clear and was found to be very similar to peptides in F3 and contactin/F11. In addition, because the human peptide was generated by endopeptidase lys-c cleavage, k is most likely flanked by lysine residues. These residues are also conserved in mouse and chicken. On the basis of the amino acid sequence similarities, it is believed that the Neuro-1 antigen is the human counterpart of F3 and contactin/F11. It is therefore referred to herein as human contactin.

cDNAs encoding the Neuro-1 antigen were cloned to confirm its identity as human contactin. Mouse F3 probes were used to screen a human neuroblastoma cDNA library (Clontech, Palo Alto, Calif.). The probes were generated by reverse transcriptase-polymerase chain reaction (RT-PCR) of mouse brain polyA+RNA using primer pairs based on the mouse F3 sequence as reported by Gennarini, et al. supra, (GENBANK locus: musF3, accession #X14943). To perform the RT-PCR, mouse brain polyA+RNA was prepared using the oligo d(T) cellulose method (Maniatis, et al. *Molecular Cloning—A Laboratory Manual*, Cold Spring Harbor Laboratory. 1982). The RT-PCR amplification reaction was based on the one-step protocol described by Goblet, et al. (1989. Nucleic Acids Res. 17:2144). PolyA+RNA (1 µg) and 300 ng of each palmer (see below) in 66 µl DEPC water were incubated at 65° C. for 15 min. and cooled on ice. Thirty-three µl of 3X RT-PCK reagent mix (3X PCK buffer, 150 mM KCl, 30 mM Tris-Cl pH 8.3, 4.5 mM MgCl$_2$, 0.3% gelatin, 500 µM dNTPs, 200 U M-MLV reverse transcriptase, 4 U rRNAsin (Promega, Madison, Wis.), 2.5 U AMPLITAQ (Perkin-Elmer Cetus, Norwalk, Conn.) was added and the reaction was incubated at 37° C. for 30 min., followed by 94° C. for 1 min, 50° C. for 2 min., and 72° C. for 2 min. The amplification reaction was repeated for 40 cycles. Palmer pairs A/B and C/D were used for amplification of the mouse F3 probes:

| PRI-MER FIG. 1 | SEQUENCE ID NO. | SEQUENCE* | NUCLEOTIDE POSITION IN musF3 |
|---|---|---|---|
| A | SEQ ID NO:3 | CTCTGGTGATCACAAATC | 1742–1759 |
| B | SEQ ID NO:4 | TCATCTGAGAGAATCGTC | 2181–2198 |
| C | SEQ ID NO:1 | TAGACCGGATGGCCAACA | 3087–3104 |
| D | SEQ ID NO:2 | CTCGACAACATACTCTCC | 3163–3180 |

*Primers B and D are inverse complements of musF3.

The probes were verified as mouse F3 by direct sequencing with SEQUENASE (United States Biochemical Corp., Cleveland, Ohio) performed as described by Mihovilovic ((1989) BioTechniques 7:14–16). This is an efficient method for sequencing PCR amplified DNA. The PCR products of primer pair SEQ ID NO: 1/SEQ ID NO:2 (94 bp) and SEQ ID NO:3/SEQ ID NO:4 (457 bp) were gel purified and re-amplified using asymmetric primer concentrations to produce the single-stranded sequencing templates.

Using the mouse SEQ 12D NO:1/SEQ ID NO:2 probe prepared above, a human Kelly neuroblastoma lambda gt10 cDNA library (Clontech, Palo Alto, Calif.) was screened as recommended by the manufacturer. Two cDNA clones were isolated, including the clone NX-7 which contained the cDNA shown in FIG. 1. To obtain clones containing upstream sequences, the neuroblastoma library was screened using the mouse SEQ ID NO:3/SEQ ID NO:4 probe. Three clones were identified from this screening, including one which was a full-length clone containing the entire coding sequence. This clone was designated clone NXII-7. Lambda cDNA inserts were either PCR amplified using lambda gt10 EcoRI forward and reverse primers and sequenced directly or subcloned into pBLUESCRIPT (SK+) (Stratagene, La Jolla, Calif.) prior to sequencing. The pBLUESCRIPT subclones were sequenced manually by either dideoxy termination with SEQUENASE or by dye-termination or dye-labeled primer automated sequencing (Applied Biosystems, Model 373A, Foster City, Calif.) as recommended by the manufacturers. Sequencing primers were synthesized on an Applied Biosystems (ABI) Model 380B DNA synthesizer and purified using OPC cartridges (ABI) as recommended. Sequence alignments, translations, and features location were performed using IG-Suite software (Intelligenetics, Mountain View, Calif.). The cDNAs produced by this procedure may be used as probes to isolate the genomic DNA coding for human contactin.

The entire human contactin cDNA coding and partial 5' and 3' untranslated sequence was determined by sequencing both strands of cDNA (SEQ ID NO:5; EMBL Accession #Z21488). Among the various cDNA clones, two single base variations were observed at positions 2424 and 2513. These result in valine to leucine and leucine to valine transitions, respectively. Human contactin cDNA contains a 3054 bp open reading frame which is capable of encoding a polypeptide 1018 amino acids in length (SEQ ID NO:6). The predicted polypeptide contains hydrophobic segments at the amino-terminal and carboxyl-terminal ends. The amino terminal hydrophobic segment contains a consensus processing site and is believed to be a signal sequence which is cleaved to yield the amino terminus of the mature polypeptide. The hydrophobic segment at the carboxyl terminus is similar to segments found at the carboxyl ends of other phosphatidylinositol-linked membrane proteins and it is believed to be removed during the attachment to glycolipid. The fact that the Neuro-1 antigen is released from the cell surface by phosphatidylinositol-specific phospholipase C is consistent with this hypothesis. Included in the predicted amino acid sequence of the polypeptide, at positions 836–850, is the sequence of the Neuro-1 antigen lys-c peptide described above, confirming that the Neuro-1 antigen is the human contactin cell adhesion molecule.

As previously disclosed, Berglund, et al. have reported a molecule designated Gp135 which they describe as a possible human homologue of mouse F3 and chicken contactin/F11. However, the Berglund, et al. internal peptide sequence is only 71% similar to the deduced amino acid sequence of a corresponding peptide (residues 679–693) of the present invention.

The deduced amino acid sequence of human contactin contains six immunoglobulin-like domains followed by four fibronectin Type III-like repeats. This structure is similar to mouse F3 and chicken contactin/F11. In the second fibronectin Type III repeat the carboxyl-terminal conserved tyrosine is replaced by phenylalanine as in mouse F3. There are nine consensus sites for asparagine-linked glycosylation, all of which are conserved between human and mouse. The deduced human and mouse polypeptide sequences are 95% homologous and differ in size by two amino acids. Mouse F3 contains a single dipeptide insert within the sixth immunoglobulin-like domain which is absent in human contactin and chicken contactin/F11. It is not known whether this sequence gap is the result of alternate RNA splicing or a reflection of intra-exonic differences between species. The regions of lowest sequence identity have about 70% homology and are located in the hydrophobic amino terminal and carboxyl-terminal segments.

Polyclonal antisera were generated in rabbits using immunoaffinity purified human contactin to further confirm that the Neuro-1 antigen is the human homologue of F3 and contactin/F11. The sera recognized the immunogen in immunoblots at a 1:12,000 dilution. The sera also reacted with a glutathione S-transferase/human contactin fusion protein expressed in bacteria. The human contactin portion of this fusion protein comprised the carboxy-terminal region of human contactin, corresponding to the cDNA in clone NX-7, cloned in pGEX-2T (Pharmacia, Piscataway, N.J.).

The upstream EcoRI fragment of the cDNA insert of NXII-7 and the entire cDNA insert of NX-7 were used as probes to characterize the expression pattern of human contactin in various tissues. Human brain contained a single major approximately 6.5 kb mRNA. This transcript is larger than is necessary to encode the human contactin protein and is believed to include a large 3' untranslated region which is not completely represented in the cDNA clones isolated. The isolated cDNAs extended no more than about 1.2 kb past the carboxyl-terminus of the human contactin molecule.

Of the other tissues tested, pancreas and lung exhibited a low level of expression (compared to brain) of the 6.8 kb transcript and a 6.0 kb doublet similar to the pattern seen in cell lines (see below). Skeletal muscle and kidney showed similar, yet very weak 6.8 and 6.0 kb transcripts. Heart and liver were negative for human contactin transcripts. The human neuroblastoma cell lines IMR-32, SK-N-MC, SMS-KAN and SK-N-SH contained human contactin mRNA, as did the retinoblastoma cell line Y79. In these cell lines, in contrast to the transcript pattern in brain, multiple RNA species were observed—a 6.8 kb species, a 6.0 kb doublet and a 4.2 kb species. It is unclear in all cases whether or not the approximately 6.8 kb and 6.5 kb transcripts are significantly different. Rhabdomyosarcoma (A204, RD and A673), hematopoietic (KG1a.5), small cell lung carcinema (SHP77) and Ewing Sarcoma (RD-ES) cell lines did not express human contactin RNA.

The antibodies which recognize human contactin and the nucleotide probes derived from the nucleotide sequence which codes for human contactin are useful in methods for detecting the protein and nucleotide sequences, respectively. Nucleotide probes may comprise the complete cloned cDNA sequence or a portion thereof. One skilled in the art will further recognize that nucleotide probes may be designed which comprise all or a portion of a sequence which is complementary to the cloned sequences. To detect the contactin protein, immunoassay methods involving binding between a protein and its antibody such as ELISAs and immunoblots can be readily adapted to employ the antibodies and contactin glycoprotein disclosed herein. These immunoassay methods are known in the art. In general, detection of binding between protein and antibody is accomplished by including a signal moiety in the binding reaction. This is usually in the form of a detectable label conjugated to the antibody or protein. The detectable label may be directly detectable (e.g., a dye, radioisotope or fluorochrome) or rendered detectable after further chemical reaction (e.g., an enzyme which reacts to produce a colored product or biotin which may be bound to labeled avidin).

Detection of nucleic acids by hybridization to a probe is also known in the art. Such methods as Southern blotting, dot blotting and the like may be readily adapted to detection of oligonucleotides containing all or part of a nucleic acid sequence encoding human contactin using the nucleotide sequence information of SEQ ID NO:5 to design appropriate probes. For purposes of the present invention, the terms "encoding" and "coding for" are intended to include nucleic acids which comprise sequences which can be transcribed and/or translated to produce human contactin. That is, both DNA and the RNA transcribed from it are considered to "code for" or "encode" human contactin. It will also be understood that probes derived from the disclosed nucleotide sequences may also be used to detect fragments of the disclosed coding sequences. As for immunoassays, hybridization of the probe to the contactin nucleotide sequence will be detected by means of a directly or indirectly detectable label associated with the probe, i.e., incorporated in the probe or conjugated to it. In general the same labels useful for labeling antibodies and antigens may be used to label oligonucleotides. In addition, it is within the ordinary skill in the art, given the nucleotide sequence of SEQ ID NO:5, to derive the complementary nucleotide sequence, which may also be used to prepare probes and which may be detected by hybridization to probes. Further, the present disclosure of SEQ ID NO:5 as a DNA sequence easily allows derivation of RNA sequences which are complementary to either SEQ ID NO:5 or its complementary strand. Such equivalent RNA sequences may be detected by hybridization to probes as well.

The reagents for performing these immunoassays and hybridization assays may be conveniently packaged together for sale or use in the form of a kit. A kit for immunoassay may contain an antibody which recognizes and binds to human contactin conjugated to a selected label and optionally any reagents necessary for performing the assay and detecting the label. A kit for a hybridization assay may contain short oligonucleotide probes which hybridize to one or more nucleotide sequences contained in SEQ ID NO:5, the probes being conjugated to the selected label. Optionally, the hybridization assay kit may contain any reagents necessary for performing the hybridization assay and detecting the label.

The foregoing disclosure is intended to illustrate the invention but is not to be construed as limiting its scope as defined by the appended claims. Upon reading the present disclosure, certain equivalents and variations will be apparent to one skilled in the art without the exercise of inventive skill and without departing from the spirit of the invention. Such equivalents and variations are intended to be included within its scope.

What is claimed is:

1. An isolated polypeptide comprising the amino acid sequence of SEQ ID NO:6.

2. The polypeptide of claim 1 which is glycosylated.

3. An isolated polypeptide having an amino acid sequence comprising amino acids 1–971 of SEQ ID NO:6.

4. The polypeptide of claim 3 which is glycosylated.

5. The polypeptide of claim 4 which is linked to phosphatidylinositol at the carboxy-terminus.

* * * * *

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: Mouse ( x i ) SEQUENCE DESCRIPTION: SEQ ID NO:1:

TAGACCGGAT GGCCAACA                                                1 8

( 2 ) INFORMATION FOR SEQ ID NO:2:

( i ) SEQUENCE CHARACTERISTICS:
   ( A ) LENGTH: 18 base pairs
   ( B ) TYPE: nucleic acid
   ( C ) STRANDEDNESS: single
   ( D ) TOPOLOGY: linear ( i i ) MOLECULE TYPE: cDNA ( i i i ) HYPOTHETICAL: NO ( i v ) ANTI-SENSE: YES ( v i ) ORIGINAL SOURCE:
   ( A ) ORGANISM: Mouse ( x i ) SEQUENCE DESCRIPTION: SEQ ID NO:2:

CTCGACAACA TACTCTCC                    18

( 2 ) INFORMATION FOR SEQ ID NO:3:

( i ) SEQUENCE CHARACTERISTICS:
      ( A ) LENGTH: 18 base pairs
      ( B ) TYPE: nucleic acid
      ( C ) STRANDEDNESS: single
      ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
      ( A ) ORGANISM: Mouse ( x i ) SEQUENCE DESCRIPTION: SEQ ID NO:3:

CTCTGGTGAT CACAAATC                    18

( 2 ) INFORMATION FOR SEQ ID NO:4:

( i ) SEQUENCE CHARACTERISTICS:
      ( A ) LENGTH: 18 base pairs
      ( B ) TYPE: nucleic acid
      ( C ) STRANDEDNESS: single
      ( D ) TOPOLOGY: linear ( i i ) MOLECULE TYPE: cDNA ( i i i ) HYPOTHETICAL: NO ( i v ) ANTI-SENSE: YES ( v i ) ORIGINAL SOURCE:
      ( A ) ORGANISM: Mouse ( x i ) SEQUENCE DESCRIPTION: SEQ ID NO:4:

TCATCTGAGA GAATCGTC                    18

( 2 ) INFORMATION FOR SEQ ID NO:5:

( i ) SEQUENCE CHARACTERISTICS:
      ( A ) LENGTH: 3360 base pairs
      ( B ) TYPE: nucleic acid
      ( C ) STRANDEDNESS: both
      ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
      ( A ) ORGANISM: Homo sapiens 5,688,916

11 12

-continued ( i x ) FEATURE:
 ( A ) NAME/KEY: CDS
 ( B ) LOCATION: 122..3175

( i x ) FEATURE:
 ( A ) NAME/KEY: mat_peptide
 ( B ) LOCATION: 182..3100

( i x ) FEATURE:
 ( A ) NAME/KEY: sig_peptide
 ( B ) LOCATION: 122..181

( i x ) FEATURE:
 ( A ) NAME/KEY: 5'UTR
 ( B ) LOCATION: 10..121

( i x ) FEATURE:
 ( A ) NAME/KEY: 3'UTR
 ( B ) LOCATION: 3176..3360

( i x ) FEATURE:
 ( A ) NAME/KEY: polyA_site
 ( B ) LOCATION: 3281..3286

( i x ) FEATURE:
 ( A ) NAME/KEY: misc_feature
 ( B ) LOCATION: 1..9
 ( D ) OTHER INFORMATION: /function="EcoRI cloning linker"
  / product="none"

( i x ) FEATURE:
 ( A ) NAME/KEY: misc_feature
 ( B ) LOCATION: 3101..3175
 ( D ) OTHER INFORMATION: /function="Attachment to
  glycolipid"
  / product="COOH-signal peptide"

( x i ) SEQUENCE DESCRIPTION: SEQ ID NO:5:

```
GAATTCCGGC TGTGCCGCAC CGAGGCGAGC AGGAGCAGGG AACAGGTGTT TAAAATTATC    60

CAACTGCCAT AGAGCTAAAT TCTTTTTTGG AAAATTGAAC CGAACTTCTA CTGAATACAA   120

G ATG AAA ATG TGG TTG CTG GTC AGT CAT CTT GTG ATA ATA TCT ATT       166
  Met Lys Met Trp Leu Leu Val Ser His Leu Val Ile Ile Ser Ile
  -20              -15                  -10

ACT ACC TGT TTA GCA GAG TTT ACA TGG TAT AGA AGA TAT GGT CAT GGA     214
Thr Thr Cys Leu Ala Glu Phe Thr Trp Tyr Arg Arg Tyr Gly His Gly
 -5              1               5                       10

GTT TCT GAG GAA GAC AAA GGA TTT GGA CCA ATT TTT GAA GAG CAG CCA     262
Val Ser Glu Glu Asp Lys Gly Phe Gly Pro Ile Phe Glu Glu Gln Pro
             15              20                       25

ATC AAT ACC ATT TAT CCA GAG GAA TCA CTG GAA GGA AAA GTC TCA CTC     310
Ile Asn Thr Ile Tyr Pro Glu Glu Ser Leu Glu Gly Lys Val Ser Leu
         30              35                  40

AAC TGT AGG GCA CGA GCC AGC CCT TTC CCG GTT TAC AAA TGG AGA ATG     358
Asn Cys Arg Ala Arg Ala Ser Pro Phe Pro Val Tyr Lys Trp Arg Met
     45              50                  55

AAT AAT GGG GAC GTT GAT CTC ACA AGT GAT CGA TAC AGT ATG GTA GGA     406
Asn Asn Gly Asp Val Asp Leu Thr Ser Asp Arg Tyr Ser Met Val Gly
 60              65                  70                       75

GGA AAC CTT GTT ATC AAC AAC CCT GAC AAA CAG AAA GAT GCT GGA ATA     454
Gly Asn Leu Val Ile Asn Asn Pro Asp Lys Gln Lys Asp Ala Gly Ile
             80              85                       90

TAC TAC TGT TTA GCA TCT AAT AAC TAC GGG ATG GTC AGA AGC ACT GAA     502
Tyr Tyr Cys Leu Ala Ser Asn Asn Tyr Gly Met Val Arg Ser Thr Glu
             95              100                      105

GCA ACC CTG AGC TTT GGA TAT CTT GAT CCT TTC CCA CCT GAG GAA CGT     550
Ala Thr Leu Ser Phe Gly Tyr Leu Asp Pro Phe Pro Pro Glu Glu Arg
         110             115                 120
```

-continued

| | | | | | | | | | | | | | | | | |
|---|---|---|---|---|---|---|---|---|---|---|---|---|---|---|---|---|
| CCT | GAG | GTC | AGA | GTA | AAA | GAA | GGG | AAA | GGA | ATG | GTG | CTT | CTC | TGT | GAC | 598 |
| Pro | Glu | Val | Arg | Val | Lys | Glu | Gly | Lys | Gly | Met | Val | Leu | Leu | Cys | Asp | |
| | 125 | | | | | 130 | | | | | 135 | | | | | |
| CCC | CCA | TAC | CAT | TTT | CCA | GAT | GAT | CTT | AGC | TAT | CGC | TGG | CTT | CTA | AAT | 646 |
| Pro | Pro | Tyr | His | Phe | Pro | Asp | Asp | Leu | Ser | Tyr | Arg | Trp | Leu | Leu | Asn | |
| 140 | | | | | 145 | | | | | 150 | | | | | 155 | |
| GAA | TTT | CCT | GTA | TTT | ATC | ACA | ATG | GAT | AAA | CGG | CGA | TTT | GTG | TCT | CAG | 694 |
| Glu | Phe | Pro | Val | Phe | Ile | Thr | Met | Asp | Lys | Arg | Arg | Phe | Val | Ser | Gln | |
| | | | | 160 | | | | | 165 | | | | | 170 | | |
| ACA | AAT | GGC | AAT | CTC | TAC | ATT | GCA | AAT | GTT | GAG | GCT | TCC | GAC | AAA | GGC | 742 |
| Thr | Asn | Gly | Asn | Leu | Tyr | Ile | Ala | Asn | Val | Glu | Ala | Ser | Asp | Lys | Gly | |
| | | | 175 | | | | 180 | | | | | 185 | | | | |
| AAT | TAT | TCC | TGC | TTT | GTT | TCC | AGT | CCT | TCT | ATT | ACA | AAG | AGC | GTG | TTC | 790 |
| Asn | Tyr | Ser | Cys | Phe | Val | Ser | Ser | Pro | Ser | Ile | Thr | Lys | Ser | Val | Phe | |
| | | 190 | | | | | 195 | | | | | 200 | | | | |
| AGC | AAA | TTC | ATC | CCA | CTC | ATT | CCA | ATA | CCT | GAA | CGA | ACA | ACA | AAA | CCA | 838 |
| Ser | Lys | Phe | Ile | Pro | Leu | Ile | Pro | Ile | Pro | Glu | Arg | Thr | Thr | Lys | Pro | |
| | 205 | | | | | 210 | | | | | 215 | | | | | |
| TAT | CCT | GCT | GAT | ATT | GTA | GTT | CAG | TTC | AAG | GAT | GTA | TAT | GCA | TTG | ATG | 886 |
| Tyr | Pro | Ala | Asp | Ile | Val | Val | Gln | Phe | Lys | Asp | Val | Tyr | Ala | Leu | Met | |
| 220 | | | | | 225 | | | | | 230 | | | | | 235 | |
| GGC | CAA | AAT | GTG | ACC | TTA | GAA | TGT | TTT | GCA | CTT | GGA | AAT | CCT | GTT | CCG | 934 |
| Gly | Gln | Asn | Val | Thr | Leu | Glu | Cys | Phe | Ala | Leu | Gly | Asn | Pro | Val | Pro | |
| | | | | 240 | | | | | 245 | | | | | 250 | | |
| GAT | ATC | CGA | TGG | CGG | AAG | GTT | CTA | GAA | CCA | ATG | CCA | AGC | ACT | GCT | GAG | 982 |
| Asp | Ile | Arg | Trp | Arg | Lys | Val | Leu | Glu | Pro | Met | Pro | Ser | Thr | Ala | Glu | |
| | | | 255 | | | | | 260 | | | | | 265 | | | |
| ATT | AGC | ACC | TCT | GGG | GCT | GTT | CTT | AAG | ATC | TTC | AAT | ATT | CAG | CTA | GAA | 1030 |
| Ile | Ser | Thr | Ser | Gly | Ala | Val | Leu | Lys | Ile | Phe | Asn | Ile | Gln | Leu | Glu | |
| | | 270 | | | | | 275 | | | | | 280 | | | | |
| GAT | GAA | GGC | ATC | TAT | GAA | TGT | GAG | GCT | GAG | AAC | ATT | AGA | GGA | AAG | GAT | 1078 |
| Asp | Glu | Gly | Ile | Tyr | Glu | Cys | Glu | Ala | Glu | Asn | Ile | Arg | Gly | Lys | Asp | |
| | 285 | | | | | 290 | | | | | 295 | | | | | |
| AAA | CAT | CAA | GCA | AGA | ATT | TAT | GTT | CAA | GCA | TTC | CCT | GAG | TGG | GTA | GAA | 1126 |
| Lys | His | Gln | Ala | Arg | Ile | Tyr | Val | Gln | Ala | Phe | Pro | Glu | Trp | Val | Glu | |
| 300 | | | | | 305 | | | | | 310 | | | | | 315 | |
| CAC | ATC | AAT | GAC | ACA | GAG | GTG | GAC | ATA | GGC | AGT | GAT | CTC | TAC | TGG | CCT | 1174 |
| His | Ile | Asn | Asp | Thr | Glu | Val | Asp | Ile | Gly | Ser | Asp | Leu | Tyr | Trp | Pro | |
| | | | | 320 | | | | | 325 | | | | | 330 | | |
| TGT | GTG | GCC | ACA | GGA | AAG | CCC | ATC | CCT | ACA | ATC | CGA | TGG | TTG | AAA | AAT | 1222 |
| Cys | Val | Ala | Thr | Gly | Lys | Pro | Ile | Pro | Thr | Ile | Arg | Trp | Leu | Lys | Asn | |
| | | | 335 | | | | | 340 | | | | | 345 | | | |
| GGA | TAT | GCG | TAT | CAT | AAA | GGG | GAA | TTA | AGA | CTG | TAT | GAT | GTG | ACT | TTT | 1270 |
| Gly | Tyr | Ala | Tyr | His | Lys | Gly | Glu | Leu | Arg | Leu | Tyr | Asp | Val | Thr | Phe | |
| | | 350 | | | | | 355 | | | | | 360 | | | | |
| GAA | AAT | GCC | GGA | ATG | TAT | CAG | TGC | ATA | GCT | GAA | AAC | ACA | TAT | GGA | GCC | 1318 |
| Glu | Asn | Ala | Gly | Met | Tyr | Gln | Cys | Ile | Ala | Glu | Asn | Thr | Tyr | Gly | Ala | |
| | 365 | | | | | 370 | | | | | 375 | | | | | |
| ATT | TAT | GCA | AAT | GCT | GAG | TTG | AAG | ATC | TTG | GCG | TTG | GCT | CCA | ACT | TTT | 1366 |
| Ile | Tyr | Ala | Asn | Ala | Glu | Leu | Lys | Ile | Leu | Ala | Leu | Ala | Pro | Thr | Phe | |
| 380 | | | | | 385 | | | | | 390 | | | | | 395 | |
| GAA | ATG | AAT | CCT | ATG | AAG | AAA | AAG | ATC | CTG | GCT | GCT | AAA | GGT | GGA | AGG | 1414 |
| Glu | Met | Asn | Pro | Met | Lys | Lys | Lys | Ile | Leu | Ala | Ala | Lys | Gly | Gly | Arg | |
| | | | | 400 | | | | | 405 | | | | | 410 | | |
| GTG | ATA | ATT | GAA | TGC | AAA | CCT | AAA | GCT | GCA | CCG | AAA | CCA | AAG | TTT | TCA | 1462 |
| Val | Ile | Ile | Glu | Cys | Lys | Pro | Lys | Ala | Ala | Pro | Lys | Pro | Lys | Phe | Ser | |
| | | | 415 | | | | | 420 | | | | | 425 | | | |
| TGG | AGT | AAA | GGG | ACA | GAG | TGG | CTT | GTC | AAT | AGC | AGC | AGA | ATA | CTC | ATT | 1510 |
| Trp | Ser | Lys | Gly | Thr | Glu | Trp | Leu | Val | Asn | Ser | Ser | Arg | Ile | Leu | Ile | |
| | | 430 | | | | | 435 | | | | | 440 | | | | |

```
TGG GAA GAT GGT AGC TTG GAA ATC AAC AAC ATT ACA AGG AAT GAT GGA    1558
Trp Glu Asp Gly Ser Leu Glu Ile Asn Asn Ile Thr Arg Asn Asp Gly
    445             450                 455

GGT ATC TAT ACA TGC TTT GCA GAA AAT AAC AGA GGG AAA GCT AAT AGC    1606
Gly Ile Tyr Thr Cys Phe Ala Glu Asn Asn Arg Gly Lys Ala Asn Ser
460             465                 470                 475

ACT GGA ACC CTT GTT ATC ACA GAT CCT ACG CGA ATT ATA TTG GCC CCA    1654
Thr Gly Thr Leu Val Ile Thr Asp Pro Thr Arg Ile Ile Leu Ala Pro
                480                 485                 490

ATT AAT GCC GAT ATC ACA GTT GGA GAA AAC GCC ACC ATG CAG TGT GCT    1702
Ile Asn Ala Asp Ile Thr Val Gly Glu Asn Ala Thr Met Gln Cys Ala
            495                 500                 505

GCG TCC TTT GAT CCT GCC TTG GAT CTC ACA TTT GTT TGG TCC TTC AAT    1750
Ala Ser Phe Asp Pro Ala Leu Asp Leu Thr Phe Val Trp Ser Phe Asn
        510                 515                 520

GGC TAT GTG ATC GAT TTT AAC AAA GAG AAT ATT CAC TAC CAG AGG AAT    1798
Gly Tyr Val Ile Asp Phe Asn Lys Glu Asn Ile His Tyr Gln Arg Asn
    525                 530                 535

TTT ATG CTG GAT TCC AAT GGG GAA TTA CTA ATC CGA AAT GCG CAG CTG    1846
Phe Met Leu Asp Ser Asn Gly Glu Leu Leu Ile Arg Asn Ala Gln Leu
540                 545                 550                 555

AAA CAT GCT GGA AGA TAC ACA TGC ACT GCC CAG ACA ATT GTG GAC AAT    1894
Lys His Ala Gly Arg Tyr Thr Cys Thr Ala Gln Thr Ile Val Asp Asn
                560                 565                 570

TCT TCA GCT TCA GCT GAC CTT GTA GTG AGA GGC CCT CCA GGC CCT CCA    1942
Ser Ser Ala Ser Ala Asp Leu Val Val Arg Gly Pro Pro Gly Pro Pro
            575                 580                 585

GGT GGT CTG AGA ATA GAA GAC ATT AGA GCC ACT TCT GTG GCA CTT ACT    1990
Gly Gly Leu Arg Ile Glu Asp Ile Arg Ala Thr Ser Val Ala Leu Thr
        590                 595                 600

TGG AGC CGT GGT TCA GAC AAT CAT AGT CCT ATT TCT AAA TAC ACT ATC    2038
Trp Ser Arg Gly Ser Asp Asn His Ser Pro Ile Ser Lys Tyr Thr Ile
605                 610                 615

CAG ACC AAG ACT ATT CTT TCA GAT GAC TGG AAA GAT GCA AAG ACA GAT    2086
Gln Thr Lys Thr Ile Leu Ser Asp Asp Trp Lys Asp Ala Lys Thr Asp
620                 625                 630                 635

CCC CCA ATT ATT GAA GGA AAT ATG GAG GCA GCA AGA GCA GTG GAC TTA    2134
Pro Pro Ile Ile Glu Gly Asn Met Glu Ala Ala Arg Ala Val Asp Leu
                640                 645                 650

ATC CCA TGG ATG GAG TAT GAA TTC CGC GTG GTA GCA ACC AAT ACA CTG    2182
Ile Pro Trp Met Glu Tyr Glu Phe Arg Val Val Ala Thr Asn Thr Leu
            655                 660                 665

GGT AGA GGA GAG CCC AGT ATA CCA TCT AAC AGA ATT AAA ACA GAC GGT    2230
Gly Arg Gly Glu Pro Ser Ile Pro Ser Asn Arg Ile Lys Thr Asp Gly
        670                 675                 680

GCT GCA CCA AAT GTG GCT CCT TCA GAT GTA GGA GGT GGA GGT AGA        2278
Ala Ala Pro Asn Val Ala Pro Ser Asp Val Gly Gly Gly Gly Gly Arg
    685                 690                 695

AAC AGA GAG CTG ACC ATA ACA TGG GCG CCT TTG TCA AGA GAA TAC CAC    2326
Asn Arg Glu Leu Thr Ile Thr Trp Ala Pro Leu Ser Arg Glu Tyr His
700                 705                 710                 715

TAT GGC AAC AAT TTT GGT TAC ATA GTG GCA TTT AAG CCA TTT GAT GGA    2374
Tyr Gly Asn Asn Phe Gly Tyr Ile Val Ala Phe Lys Pro Phe Asp Gly
                720                 725                 730

GAA GAA TGG AAA AAA GTC ACA GTT ACT AAT CCT GAT ACT GGC CGA TAT    2422
Glu Glu Trp Lys Lys Val Thr Val Thr Asn Pro Asp Thr Gly Arg Tyr
            735                 740                 745

GTC CAT AAA GAT GAA ACC ATG AGC CCT TCC ACT GCA TTT CAA GTT AAA    2470
Val His Lys Asp Glu Thr Met Ser Pro Ser Thr Ala Phe Gln Val Lys
        750                 755                 760
```

```
GTC AAG GCC TTC AAC AAC AAA GGA GAT GGA CCT TAC AGC CTA CTA GCA      2518
Val Lys Ala Phe Asn Asn Lys Gly Asp Gly Pro Tyr Ser Leu Leu Ala
765             770                 775

GTC ATT AAT TCA GCA CAA GAC GCT CCC AGT GAA GCC CCA ACA GAA GTA      2566
Val Ile Asn Ser Ala Gln Asp Ala Pro Ser Glu Ala Pro Thr Glu Val
780             785                 790                 795

GGT GTA AAA GTC TTA TCA TCT TCT GAG ATA TCT GTT CAT TGG GAA CAT      2614
Gly Val Lys Val Leu Ser Ser Ser Glu Ile Ser Val His Trp Glu His
                800                 805                 810

GTT TTA GAA AAA ATA GTG GAA AGC TAT CAG ATT CGG TAT TGG GCT GCC      2662
Val Leu Glu Lys Ile Val Glu Ser Tyr Gln Ile Arg Tyr Trp Ala Ala
            815                 820                 825

CAT GAC AAA GAA GAA GCT GCA AAC AGA GTT CAA GTC ACC AGC CAA GAG      2710
His Asp Lys Glu Glu Ala Ala Asn Arg Val Gln Val Thr Ser Gln Glu
        830                 835                 840

TAC TCG GCC AGG CTC GAG AAC CTT CTG CCA GAC ACC CAG TAT TTT ATA      2758
Tyr Ser Ala Arg Leu Glu Asn Leu Leu Pro Asp Thr Gln Tyr Phe Ile
    845                 850                 855

GAA GTC GGG GCC TGC AAT AGT GCA GGG TGT GGA CCT CCA AGT GAC ATG      2806
Glu Val Gly Ala Cys Asn Ser Ala Gly Cys Gly Pro Pro Ser Asp Met
860                 865                 870                 875

ATT GAG GCT TTC ACC AAG AAA GCA CCT CCT AGC CAG CCT CCA AGG ATC      2854
Ile Glu Ala Phe Thr Lys Lys Ala Pro Pro Ser Gln Pro Pro Arg Ile
                880                 885                 890

ATC AGT TCA GTA AGG TCT GGT TCA CGC TAT ATA ATC ACC TGG GAT CAT      2902
Ile Ser Ser Val Arg Ser Gly Ser Arg Tyr Ile Ile Thr Trp Asp His
            895                 900                 905

GTC GTT GCA CTA TCA AAT GAA TCT ACA GTG ACG GGA TAT AAG GTA CTC      2950
Val Val Ala Leu Ser Asn Glu Ser Thr Val Thr Gly Tyr Lys Val Leu
        910                 915                 920

TAC AGA CCT GAT GGC CAG CAT GAT GGC AAG CTG TAT TCA ACT CAC AAA      2998
Tyr Arg Pro Asp Gly Gln His Asp Gly Lys Leu Tyr Ser Thr His Lys
    925                 930                 935

CAC TCC ATA GAA GTC CCA ATC CCC AGA GAT GGA GAA TAC GTT GTG GAG      3046
His Ser Ile Glu Val Pro Ile Pro Arg Asp Gly Glu Tyr Val Val Glu
940                 945                 950                 955

GTT CGC GCG CAC AGT GAT GGA GGA GAT GGA GTG GTG TCT CAA GTC AAA      3094
Val Arg Ala His Ser Asp Gly Gly Asp Gly Val Val Ser Gln Val Lys
                960                 965                 970

ATT TCA GGT GCA CCC ACC CTA TCC CCA AGT CTT CTC GGC TTA CTG CTG      3142
Ile Ser Gly Ala Pro Thr Leu Ser Pro Ser Leu Leu Gly Leu Leu Leu
            975                 980                 985

CCT GCC TTT GGC ATC CTT GTC TAC TTG GAA TTC TGAATGTGTT GTGACAGCTG    3195
Pro Ala Phe Gly Ile Leu Val Tyr Leu Glu Phe
        990                 995

CTGTTCCCAT CCCAGCTCAG AAGACACCCT TCAACCCTGG GATGACCACA ATTCCTTCCA    3255

ATTTCTGCGG CTCCATCCTA AGCCAAATAA ATTATACTTT AACAAACTAT TCAACTGATT    3315

TACAACACAC ATGATGACTG AGGCATTCAG GAACCCCTTC ATCCA                    3360
```

( 2 ) INFORMATION FOR SEQ ID NO:6:

( i ) SEQUENCE CHARACTERISTICS:
        ( A ) LENGTH: 1018 amino acids
        ( B ) TYPE: amino acid
        ( D ) TOPOLOGY: linear ( i i ) MOLECULE TYPE: protein ( v i ) ORIGINAL SOURCE:
        ( A ) ORGANISM: Homo sapiens ( i x ) FEATURE:
    ( A ) NAME/KEY: Disulfide-bond
    ( B ) LOCATION: 45..94

( i x ) FEATURE:
    ( A ) NAME/KEY: Disulfide-bond
    ( B ) LOCATION: 138..191

( i x ) FEATURE:
    ( A ) NAME/KEY: Disulfide-bond
    ( B ) LOCATION: 243..290

( i x ) FEATURE:
    ( A ) NAME/KEY: Disulfide-bond
    ( B ) LOCATION: 332..371

( i x ) FEATURE:
    ( A ) NAME/KEY: Disulfide-bond
    ( B ) LOCATION: 416..464

( i x ) FEATURE:
    ( A ) NAME/KEY: Disulfide-bond
    ( B ) LOCATION: 506..563

( i x ) FEATURE:
    ( A ) NAME/KEY: Domain
    ( B ) LOCATION: 604..657
    ( D ) OTHER INFORMATION: /label=FLR
        / note="conserved core of fibronectin type
        III-like repeat"

( i x ) FEATURE:
    ( A ) NAME/KEY: Domain
    ( B ) LOCATION: 707..760
    ( D ) OTHER INFORMATION: /label=FLR
        / note="conserved core of fibronectin type
        III-like repeat"

( i x ) FEATURE:
    ( A ) NAME/KEY: Domain
    ( B ) LOCATION: 809..857
    ( D ) OTHER INFORMATION: /label=FLR
        / note="conserved core of fibronectin type
        III-like repeat"

( i x ) FEATURE:
    ( A ) NAME/KEY: Domain
    ( B ) LOCATION: 905..952
    ( D ) OTHER INFORMATION: /label=FLR
        / note="conserved core of fibronectin type
        III-like repeat"

( i x ) FEATURE:
    ( A ) NAME/KEY: Modified-site
    ( B ) LOCATION: 188
    ( D ) OTHER INFORMATION: /label=ASN-glycos
        / note="potential site of ASN-linked
        glycosylation"

( i x ) FEATURE:
    ( A ) NAME/KEY: Modified-site
    ( B ) LOCATION: 238
    ( D ) OTHER INFORMATION: /label=ASN-glycos
        / note="potential site of ASN-linked
        glycosylation"

( i x ) FEATURE:
    ( A ) NAME/KEY: Modified-site
    ( B ) LOCATION: 318
    ( D ) OTHER INFORMATION: /label=ASN-glycos
        / note="potential site of ASN-linked
        glycosylation"

( i x ) FEATURE:
    ( A ) NAME/KEY: Modified-site
    ( B ) LOCATION: 437
    ( D ) OTHER INFORMATION: /label=ASN-glycos
        / note="potential site of ASN-linked
        glycosylation"

( i x ) FEATURE:
    ( A ) NAME/KEY: Modified-site
    ( B ) LOCATION: 453
    ( D ) OTHER INFORMATION: /label=ASN-glycos
        / note="potential site of ASN-linked
        glycosylation"

( i x ) FEATURE:
    ( A ) NAME/KEY: Modified-site
    ( B ) LOCATION: 474
    ( D ) OTHER INFORMATION: /label=ASN-glycos
        / note="potential site of ASN-linked
        glycosylation"

( i x ) FEATURE:
    ( A ) NAME/KEY: Modified-site
    ( B ) LOCATION: 501
    ( D ) OTHER INFORMATION: /label=ASN-glycos
        / note="potential site of ASN-linked
        glycosylation"

( i x ) FEATURE:
    ( A ) NAME/KEY: Modified-site
    ( B ) LOCATION: 571
    ( D ) OTHER INFORMATION: /label=ASN-glycos
        / note="potential site of ASN-linked
        glycosylation"

( i x ) FEATURE:
    ( A ) NAME/KEY: Modified-site
    ( B ) LOCATION: 913
    ( D ) OTHER INFORMATION: /label=ASN-glycos
        / note="potential site of ASN-linked
        glycosylation"

( x i ) SEQUENCE DESCRIPTION: SEQ ID NO:6:

| Met | Lys | Met | Trp | Leu | Leu | Val | Ser | His | Leu | Val | Ile | Ile | Ser | Ile | Thr |
|-----|-----|-----|-----|-----|-----|-----|-----|-----|-----|-----|-----|-----|-----|-----|-----|
| -20 |     |     |     |     | -15 |     |     |     | -10 |     |     |     |     |     | -5  |
| Thr | Cys | Leu | Ala | Glu | Phe | Thr | Trp | Tyr | Arg | Arg | Tyr | Gly | His | Gly | Val |
|     |     |     |     | 1   |     |     |     | 5   |     |     |     |     | 10  |     |     |
| Ser | Glu | Glu | Asp | Lys | Gly | Phe | Gly | Pro | Ile | Phe | Glu | Glu | Gln | Pro | Ile |
|     |     | 15  |     |     |     |     | 20  |     |     |     |     | 25  |     |     |     |
| Asn | Thr | Ile | Tyr | Pro | Glu | Glu | Ser | Leu | Glu | Gly | Lys | Val | Ser | Leu | Asn |
|     | 30  |     |     |     |     | 35  |     |     |     |     | 40  |     |     |     |     |
| Cys | Arg | Ala | Arg | Ala | Ser | Pro | Phe | Pro | Val | Tyr | Lys | Trp | Arg | Met | Asn |
| 45  |     |     |     |     | 50  |     |     |     |     | 55  |     |     |     |     | 60  |
| Asn | Gly | Asp | Val | Asp | Leu | Thr | Ser | Asp | Arg | Tyr | Ser | Met | Val | Gly | Gly |
|     |     |     |     | 65  |     |     |     |     | 70  |     |     |     |     | 75  |     |
| Asn | Leu | Val | Ile | Asn | Asn | Pro | Asp | Lys | Gln | Lys | Asp | Ala | Gly | Ile | Tyr |
|     |     |     | 80  |     |     |     |     | 85  |     |     |     |     | 90  |     |     |
| Tyr | Cys | Leu | Ala | Ser | Asn | Asn | Tyr | Gly | Met | Val | Arg | Ser | Thr | Glu | Ala |
|     |     | 95  |     |     |     |     | 100 |     |     |     |     | 105 |     |     |     |
| Thr | Leu | Ser | Phe | Gly | Tyr | Leu | Asp | Pro | Phe | Pro | Pro | Glu | Glu | Arg | Pro |
|     | 110 |     |     |     |     | 115 |     |     |     |     | 120 |     |     |     |     |
| Glu | Val | Arg | Val | Lys | Glu | Gly | Lys | Gly | Met | Val | Leu | Leu | Cys | Asp | Pro |
| 125 |     |     |     |     | 130 |     |     |     |     | 135 |     |     |     |     | 140 |
| Pro | Tyr | His | Phe | Pro | Asp | Asp | Leu | Ser | Tyr | Arg | Trp | Leu | Leu | Asn | Glu |
|     |     |     |     | 145 |     |     |     |     | 150 |     |     |     |     | 155 |     |
| Phe | Pro | Val | Phe | Ile | Thr | Met | Asp | Lys | Arg | Arg | Phe | Val | Ser | Gln | Thr |
|     |     |     | 160 |     |     |     |     | 165 |     |     |     |     | 170 |     |     |
| Asn | Gly | Asn | Leu | Tyr | Ile | Ala | Asn | Val | Glu | Ala | Ser | Asp | Lys | Gly | Asn |
|     |     | 175 |     |     |     |     | 180 |     |     |     |     | 185 |     |     |     |
| Tyr | Ser | Cys | Phe | Val | Ser | Ser | Pro | Ser | Ile | Thr | Lys | Ser | Val | Phe | Ser |
|     | 190 |     |     |     |     | 195 |     |     |     |     | 200 |     |     |     |     |
| Lys | Phe | Ile | Pro | Leu | Ile | Pro | Ile | Pro | Glu | Arg | Thr | Thr | Lys | Pro | Tyr |

-continued

| 205 | | | | | 210 | | | | | 215 | | | | | 220 |
|---|---|---|---|---|---|---|---|---|---|---|---|---|---|---|---|
| Pro | Ala | Asp | Ile | Val 225 | Val | Gln | Phe | Lys | Asp 230 | Val | Tyr | Ala | Leu | Met 235 | Gly |
| Gln | Asn | Val | Thr 240 | Leu | Glu | Cys | Phe | Ala 245 | Leu | Gly | Asn | Pro | Val 250 | Pro | Asp |
| Ile | Arg | Trp 255 | Arg | Lys | Val | Leu | Glu 260 | Pro | Met | Pro | Ser | Thr 265 | Ala | Glu | Ile |
| Ser | Thr 270 | Ser | Gly | Ala | Val | Leu 275 | Lys | Ile | Phe | Asn | Ile 280 | Gln | Leu | Glu | Asp |
| Glu 285 | Gly | Ile | Tyr | Glu | Cys 290 | Glu | Ala | Glu | Asn | Ile 295 | Arg | Gly | Lys | Asp | Lys 300 |
| His | Gln | Ala | Arg | Ile 305 | Tyr | Val | Gln | Ala | Phe 310 | Pro | Glu | Trp | Val | Glu 315 | His |
| Ile | Asn | Asp | Thr 320 | Glu | Val | Asp | Ile | Gly 325 | Ser | Asp | Leu | Tyr | Trp 330 | Pro | Cys |
| Val | Ala | Thr 335 | Gly | Lys | Pro | Ile | Pro 340 | Thr | Ile | Arg | Trp | Leu 345 | Lys | Asn | Gly |
| Tyr | Ala 350 | Tyr | His | Lys | Gly | Glu 355 | Leu | Arg | Leu | Tyr | Asp 360 | Val | Thr | Phe | Glu |
| Asn 365 | Ala | Gly | Met | Tyr | Gln 370 | Cys | Ile | Ala | Glu | Asn 375 | Thr | Tyr | Gly | Ala | Ile 380 |
| Tyr | Ala | Asn | Ala | Glu 385 | Leu | Lys | Ile | Leu | Ala 390 | Leu | Ala | Pro | Thr | Phe 395 | Glu |
| Met | Asn | Pro | Met 400 | Lys | Lys | Lys | Ile | Leu 405 | Ala | Ala | Lys | Gly | Gly 410 | Arg | Val |
| Ile | Ile | Glu 415 | Cys | Lys | Pro | Lys | Ala 420 | Ala | Pro | Lys | Pro | Lys 425 | Phe | Ser | Trp |
| Ser | Lys 430 | Gly | Thr | Glu | Trp | Leu 435 | Val | Asn | Ser | Ser | Arg 440 | Ile | Leu | Ile | Trp |
| Glu 445 | Asp | Gly | Ser | Leu | Glu 450 | Ile | Asn | Asn | Ile | Thr 455 | Arg | Asn | Asp | Gly | Gly 460 |
| Ile | Tyr | Thr | Cys | Phe 465 | Ala | Glu | Asn | Asn | Arg 470 | Gly | Lys | Ala | Asn | Ser 475 | Thr |
| Gly | Thr | Leu | Val 480 | Ile | Thr | Asp | Pro | Thr 485 | Arg | Ile | Ile | Leu | Ala 490 | Pro | Ile |
| Asn | Ala | Asp | Ile 495 | Thr | Val | Gly | Glu | Asn 500 | Ala | Thr | Met | Gln 505 | Cys | Ala | Ala |
| Ser | Phe 510 | Asp | Pro | Ala | Leu | Asp 515 | Leu | Thr | Phe | Val | Trp 520 | Ser | Phe | Asn | Gly |
| Tyr 525 | Val | Ile | Asp | Phe | Asn 530 | Lys | Glu | Asn | Ile | His 535 | Tyr | Gln | Arg | Asn | Phe 540 |
| Met | Leu | Asp | Ser | Asn 545 | Gly | Glu | Leu | Leu | Ile 550 | Arg | Asn | Ala | Gln | Leu 555 | Lys |
| His | Ala | Gly | Arg 560 | Tyr | Thr | Cys | Thr | Ala 565 | Gln | Thr | Ile | Val | Asp 570 | Asn | Ser |
| Ser | Ala | Ser 575 | Ala | Asp | Leu | Val | Val 580 | Arg | Gly | Pro | Pro | Gly 585 | Pro | Pro | Gly |
| Gly | Leu 590 | Arg | Ile | Glu | Asp | Ile 595 | Arg | Ala | Thr | Ser | Val 600 | Ala | Leu | Thr | Trp |
| Ser 605 | Arg | Gly | Ser | Asp | Asn 610 | His | Ser | Pro | Ile | Ser 615 | Lys | Tyr | Thr | Ile 620 | Gln |
| Thr | Lys | Thr | Ile | Leu 625 | Ser | Asp | Asp | Trp | Lys 630 | Asp | Ala | Lys | Thr 635 | Asp | Pro |

```
Pro  Ile  Ile  Glu  Gly  Asn  Met  Glu  Ala  Ala  Arg  Ala  Val  Asp  Leu  Ile
               640                           645                     650

Pro  Trp  Met  Glu  Tyr  Glu  Phe  Arg  Val  Val  Ala  Thr  Asn  Thr  Leu  Gly
          655                      660                     665

Arg  Gly  Glu  Pro  Ser  Ile  Pro  Ser  Asn  Arg  Ile  Lys  Thr  Asp  Gly  Ala
     670                      675                     680

Ala  Pro  Asn  Val  Ala  Pro  Ser  Asp  Val  Gly  Gly  Gly  Gly  Gly  Arg  Asn
685                      690                 695                          700

Arg  Glu  Leu  Thr  Ile  Thr  Trp  Ala  Pro  Leu  Ser  Arg  Glu  Tyr  His  Tyr
                    705                      710                          715

Gly  Asn  Asn  Phe  Gly  Tyr  Ile  Val  Ala  Phe  Lys  Pro  Phe  Asp  Gly  Glu
               720                      725                     730

Glu  Trp  Lys  Lys  Val  Thr  Val  Thr  Asn  Pro  Asp  Thr  Gly  Arg  Tyr  Val
          735                      740                     745

His  Lys  Asp  Glu  Thr  Met  Ser  Pro  Ser  Thr  Ala  Phe  Gln  Val  Lys  Val
     750                      755                     760

Lys  Ala  Phe  Asn  Asn  Lys  Gly  Asp  Gly  Pro  Tyr  Ser  Leu  Leu  Ala  Val
765                      770                     775                     780

Ile  Asn  Ser  Ala  Gln  Asp  Ala  Pro  Ser  Glu  Ala  Pro  Thr  Glu  Val  Gly
                    785                      790                     795

Val  Lys  Val  Leu  Ser  Ser  Ser  Glu  Ile  Ser  Val  His  Trp  Glu  His  Val
               800                      805                     810

Leu  Glu  Lys  Ile  Val  Glu  Ser  Tyr  Gln  Ile  Arg  Tyr  Trp  Ala  Ala  His
          815                      820                     825

Asp  Lys  Glu  Glu  Ala  Ala  Asn  Arg  Val  Gln  Val  Thr  Ser  Gln  Glu  Tyr
     830                      835                     840

Ser  Ala  Arg  Leu  Glu  Asn  Leu  Leu  Pro  Asp  Thr  Gln  Tyr  Phe  Ile  Glu
845                      850                     855                     860

Val  Gly  Ala  Cys  Asn  Ser  Ala  Gly  Cys  Gly  Pro  Pro  Ser  Asp  Met  Ile
               865                      870                          875

Glu  Ala  Phe  Thr  Lys  Lys  Ala  Pro  Pro  Ser  Gln  Pro  Pro  Arg  Ile  Ile
               880                      885                     890

Ser  Ser  Val  Arg  Ser  Gly  Ser  Arg  Tyr  Ile  Ile  Thr  Trp  Asp  His  Val
          895                      900                     905

Val  Ala  Leu  Ser  Asn  Glu  Ser  Thr  Val  Thr  Gly  Tyr  Lys  Val  Leu  Tyr
910                      915                     920

Arg  Pro  Asp  Gly  Gln  His  Asp  Gly  Lys  Leu  Tyr  Ser  Thr  His  Lys  His
925                      930                     935                     940

Ser  Ile  Glu  Val  Pro  Ile  Pro  Arg  Asp  Gly  Glu  Tyr  Val  Val  Glu  Val
               945                      950                     955

Arg  Ala  His  Ser  Asp  Gly  Gly  Asp  Gly  Val  Val  Ser  Gln  Val  Lys  Ile
               960                      965                     970

Ser  Gly  Ala  Pro  Thr  Leu  Ser  Pro  Ser  Leu  Leu  Gly  Leu  Leu  Leu  Pro
          975                      980                     985

Ala  Phe  Gly  Ile  Leu  Val  Tyr  Leu  Glu  Phe
     990                      995
```